(12) United States Patent
Dale et al.

(10) Patent No.: US 6,632,340 B2
(45) Date of Patent: Oct. 14, 2003

(54) PRECAST GEL AND TRAY COMBINATION FOR SUBMERGED GEL ELECTROPHORESIS

(75) Inventors: Emily C. Dale, Martinez, CA (US); Paul Feinstein, Berkeley, CA (US); Paul Zoller, Fairfield, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 09/816,738

(22) Filed: Mar. 23, 2001

(65) Prior Publication Data

US 2002/0134681 A1 Sep. 26, 2002

(51) Int. Cl.[7] .................. C02F 1/40; C02F 11/00; C25B 11/00; C25B 13/00; C25B 9/00
(52) U.S. Cl. ............................................... 204/620
(58) Field of Search ............................. 204/620

(56) References Cited

U.S. PATENT DOCUMENTS

| | | | | |
|---|---|---|---|---|
| 3,856,656 A | * | 12/1974 | Brink ......................... | 204/616 |
| 4,663,015 A | * | 5/1987 | Sleeter et al. ............... | 204/618 |
| 4,915,811 A | * | 4/1990 | Yamamoto et al. ......... | 204/619 |
| 5,411,657 A | * | 5/1995 | Leka .......................... | 204/612 |
| 5,476,016 A | * | 12/1995 | Fedorka-Cray et al. ..... | 378/162 |
| 5,543,023 A | * | 8/1996 | Lugojan ..................... | 204/618 |
| 5,767,196 A | | 6/1998 | Kozulic | |
| 5,938,906 A | * | 8/1999 | Moi et al. .................... | 204/465 |
| 6,093,301 A | * | 7/2000 | Van Atta ..................... | 204/616 |

FOREIGN PATENT DOCUMENTS

| | | | | |
|---|---|---|---|---|
| WO | PCT/US98/10004 | * | 11/1998 | ......... G01N/27/447 |

OTHER PUBLICATIONS

Michael Brush, "Laid out flat: Mini horizontal electrophoresis Devices," *The Scientist* (1998) 12(23): 16.
Michael Brush, "Cast of new players: A profile of new precast gels for nucleic acid analysis," *Scientist* (1999) 13(12): 15.
Michael Brush, "Prepare to cast off: A profile of precast acrylamide gels," *The Scientist* (1998) 12(15): 18.
"Scientific Equipment Repair: Electrophoresis," www.scientific–equipment.com/equipment/Electrophoresis/ (Feb. 14, 2001).

* cited by examiner

*Primary Examiner*—Mark L. Bell
*Assistant Examiner*—Jennine M. Brown
(74) *Attorney, Agent, or Firm*—Townsend & Townsend & Crew LLP

(57) ABSTRACT

A precast slab gel for use in submerged ("submarine") horizontal electrophoresis is formed in a tray that includes a flat base and two raised walls on opposing sides of the base, the walls containing one or more tabs on their outer surfaces, the tabs mating with grooves in the interior walls of the tank. The mating of the tabs with the grooves prevents movement and floating of the tray within to the electrophoresis cell during use. The tabs are designed to mate with grooves that are present in the tank for other purposes, which adds to the versatility of the design. Further versatility is achieved by joining the tabs to the tray walls by thin webs, which make the tabs readily removable, thereby rendering the tray usable in cell tanks that do not contain grooves. Further aspects of the invention include pins or posts extending upward from the tray base to anchor the gel, and the printing of indicia on the tray base by hot foil stamping, with the discovery that indicia printed in this manner are capable of producing a fluorescent image as part of the image produced by fluorescent-dyed protein spots in the electropherogram.

8 Claims, 4 Drawing Sheets

PRECAST GEL AND TRAY COMBINATION FOR SUBMERGED GEL ELECTROPHORESIS

BACKGROUND OF THE INVENTION

1. Field of the Invention

This invention resides in the field of laboratory apparatus for performing electrophoresis in a horizontally oriented slab gel submerged in a liquid buffer solution.

2. Description of the Prior Art

The technology of electrophoresis to separate proteins, nucleic acids, or other charged species in biological mixtures of various sorts has now developed into systems and methods that employ a wide variety of geometries and techniques. One of the most common forms of electrophoresis and one that is among the simplest to use, particularly for the analysis of nucleic acids, is electrophoresis in a horizontally oriented slab gel which is submerged in a liquid buffer solution. This is commonly known as "submerged gel electrophoresis" or "submarine electrophoresis." Horizontal systems offer the advantage of a convenient arrangement of anode and cathode buffer reservoirs along two opposing edges of the gel and an ease of placing the gel in the electrophoresis cell and removing the gel once the separation has been completed. Submarine systems arose from the discovery that a proper and controllable current could be maintained between opposing edges of the gel even when a single buffer solution occupies the reservoirs along both edges and continues in a thin layer along the top surface of the gel. Among the many advantages of submarine systems are that the upper surface of the gel can be left exposed, which facilitates its removal or allows the user to stain the gel without removing it. Agarose gels are commonly used in these systems, although other conventional electrophoresis gels can be used as well.

Submarine electrophoresis cells are commercially available from many suppliers, each having its own unique characteristics. A typical construction includes a tank and lid with appropriate electrical connections to impose a voltage within the tank, the tank molded to include a pair of elongated wells for the electrodes, the wells separated by a raised platform which supports the gel. The electrodes are supported in each well are at a height below the level of the platform. A problem that arises with cells of this type is that when the tanks are filled with enough buffer solution to submerge the gel, the gel has a tendency to move or float during sample loading and during electrophoresis, and this movement or floating can affect the results. If uncontrolled, the drift can be detrimental to reproducibility and can result in the loss of a run.

The gels used in submarine electrophoresis cells can either be formed in the cell itself, in which they are cast by the user in trays, or they can be precast by a supplier in trays which are then placed inside the cell. Precast gels offer numerous advantages, including the elimination of operator error or variation in the casting of the gel as well as a considerable reduction in time and labor involved in setting up and performing an electrophoretic separation. Unfortunately, both gels that are cast by the user in the cell and gels that are precast are susceptible to the movement and floating.

BRIEF SUMMARY OF THE INVENTION

The factors noted above and others arising in the design and use of submarine electrophoresis cells are addressed by the present invention, which resides in a precast electrophoresis gel and the tray in which the gel is cast, the tray containing features that prevent the lateral drift of the gel during electrophoresis and stabilize both the gel and tray during sample loading and electrophoresis. Like trays of the prior art, the tray of the present invention has a flat base and raised walls on two opposing sides, leaving the remaining two sides open for electrical contact with the anode and cathode through the intervening buffer solution. Unlike the prior art, however, the tray contains one or more tabs extending outward from the exterior surface(s) of the raised wall(s), the tabs mating with grooves in the interior walls of the tank. With the tabs inserted in the grooves, the lateral drift of the tray is prevented from occurring. The tabs are readily designed to mate with grooves that are present in the tank for other purposes, which adds to the versatility of the design. Further versatility is achieved by tabs that are readily removable, thereby rendering the tray usable in cell tanks that do not contain grooves.

This invention also resides in a series of protrusions or posts extending upward from the base of the tray, designed such that when a gel is cast in the tray the posts hold the gel in place and prevent it from moving within the tray. In a still further aspect, the invention resides in the inclusion of fluorescent indicia printed on the base of the tray to assist in the identification or differentiation of individual samples, or to indicate the distance of migration of components in individual samples, or both. The indicia are applied by a printing process that includes hot foil stamping. These and other features and aspects of the invention will be better understood by the description that follows.

DETAILED DESCRIPTION OF THE INVENTION AND SPECIFIC EMBODIMENTS

Figure 1:
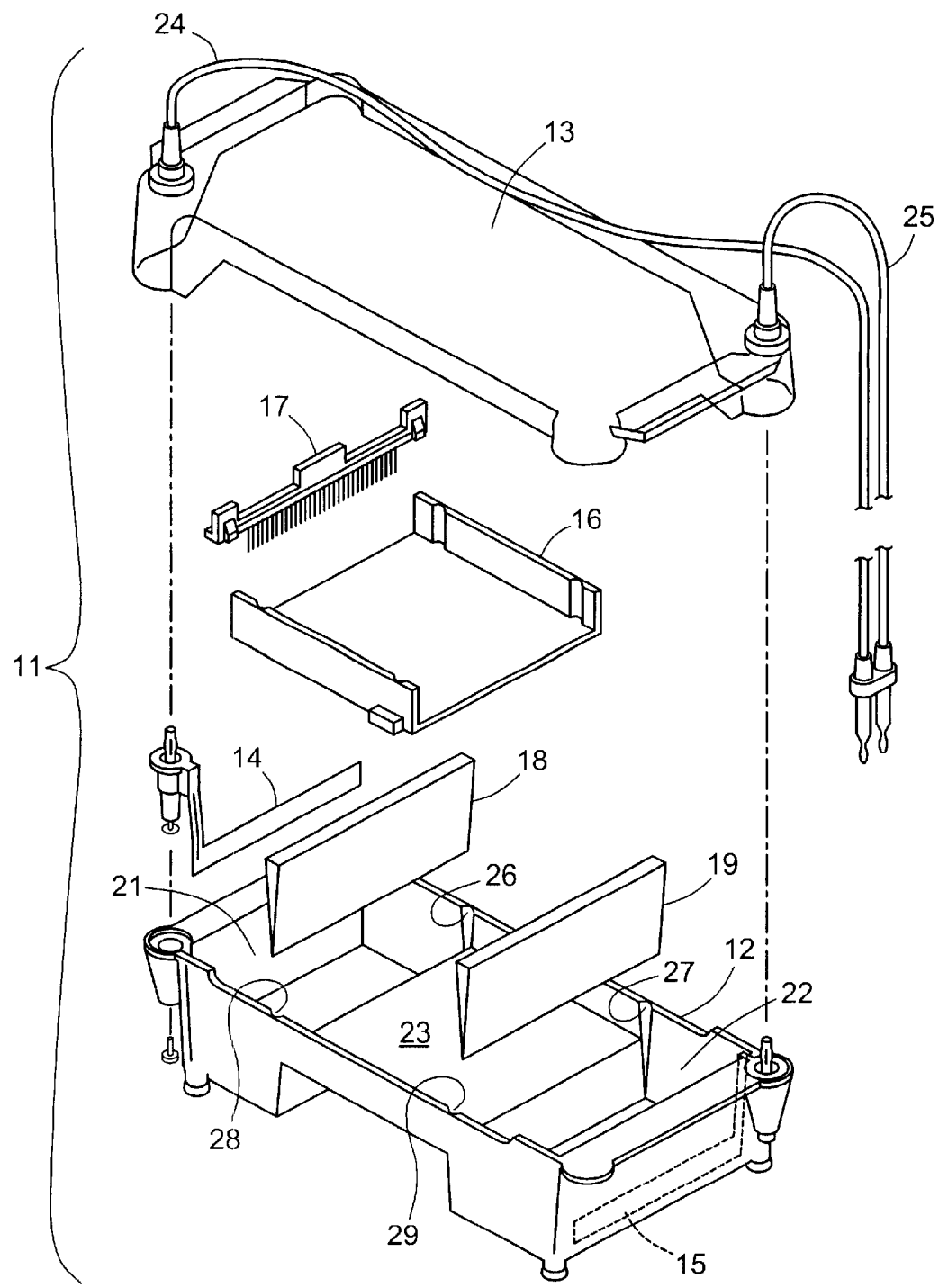
FIG. 1 is a perspective view, with parts broken away for enhanced visibility, of an electrophoresis cell in which the precast gel and tray of the invention may be used.

While the features and principles that characterize this invention and distinguish it over the prior art may be implemented in a variety of ways and embodied in a variety of constructions, the invention as a whole can best be understood by examination of a specific example. One such example is depicted in the drawings.

FIG. 1 depicts a submarine electrophoresis cell 11 that is designed for casting a gel directly within the cell rather than for use with a precast gel, but is nevertheless a cell in which the precast gel and tray of the present invention can be used. The various parts of the cell are shown in exploded form: the tank 12, the lid 13, the electrodes 14, 15 (one of which 14 is shown above the tank and the other 15 in position inside the tank), the gel tray 16, the "comb" 17 (i.e., the molding element that is inserted in the gel liquid during casting of the gel to form wells for the various samples), and the casting gates 18, 19 that are used for casting gels directly in the cell. The tank 11 is shaped to form two buffer reservoirs 21, 22 separated by a platform 23 which serves as a support for the horizontally oriented gel. One of the electrodes 14, 15 resides in each of the two buffer reservoirs, and electrical connections 24, 25 which supply voltage to the electrodes are in the lid 13. To accommodate the in-cell casting of a gel, the two removable casting gates 18, 19 are included to serve as dams for the gel-forming liquid. The gates fit into grooves 26, 27, 28, 29 in the interior walls of the tank, one groove at each of the four corners of the gel platform 23. The gates and the grooves all have complementary wedge-shaped profiles to facilitate the sliding insertion of the gates into the grooves and to stabilize the positions of the gates after they are fully inserted. In-cell casting is performed by inserting the gates in the grooves, pouring the gel-forming solution onto the surface of the platform 23 while the gates prevent the solution from spilling over into the buffer reservoirs 21, 22, placing the comb 17 in position with its teeth protruding into the gel solution and allowing the gel to solidify, then removing the gates and the comb from the cell. The samples are then placed in the wells, the lid 13 is placed over the tank, electrical connections are made, and the electrophoretic separation is begun.

The in-cell gel casting procedure described above may be performed on a gel tray that rests on the platform 23 rather than being performed directly on the platform. When a gel tray is used for this purpose, the tray fits between the gates 18, 19 during casting, and remains in place after the gates are removed to permit electrophoresis to proceed. Alternatively, the gel can be cast in a tray that is held in a separate gel casting stand that includes its own gates, similar to those shown in the drawing. The gel and tray will be held on the stand until the solution solidifies, then gel and tray are removed from the stand together and placed in the cell. In either case, once electrophoresis is completed, the tray and gel are easily removed together from the cell and the gel is stained and read directly in the tray. In the present invention, the tray which is typically used for a user-cast gel casting is not used. Instead, the precast gel and tray of the invention are substituted for, and have slightly different dimensions from, the user-cast gel (and its accompanying tray). The tray of the present invention does however make use of the wedge-shaped grooves 26, 27, 28, 29 even though these grooves are designed for use with the gates 18, 19 (which are not used in the present invention), as will be seen from the description that follows.

Figure 2:
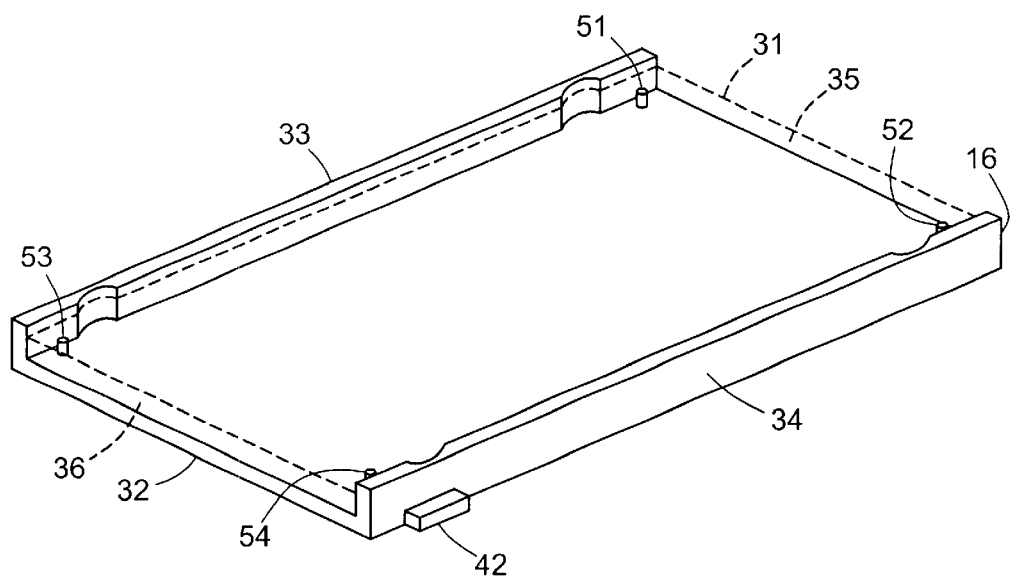
FIG. 2 is a perspective view of a precast gel and tray in accordance with the present invention.

FIG. 2 depicts a precast gel 31 and tray 16 in accordance with the present invention. The gel 31 is shown in dashed lines. The tray 16 consists of a flat rectangular base 32 and two raised walls 33, 34, one on each of two opposing parallel sides of the rectangular base. The gel 31 has exposed edges on the two other sides 35, 36 for electrical contact with the running buffer.

Figure 3:
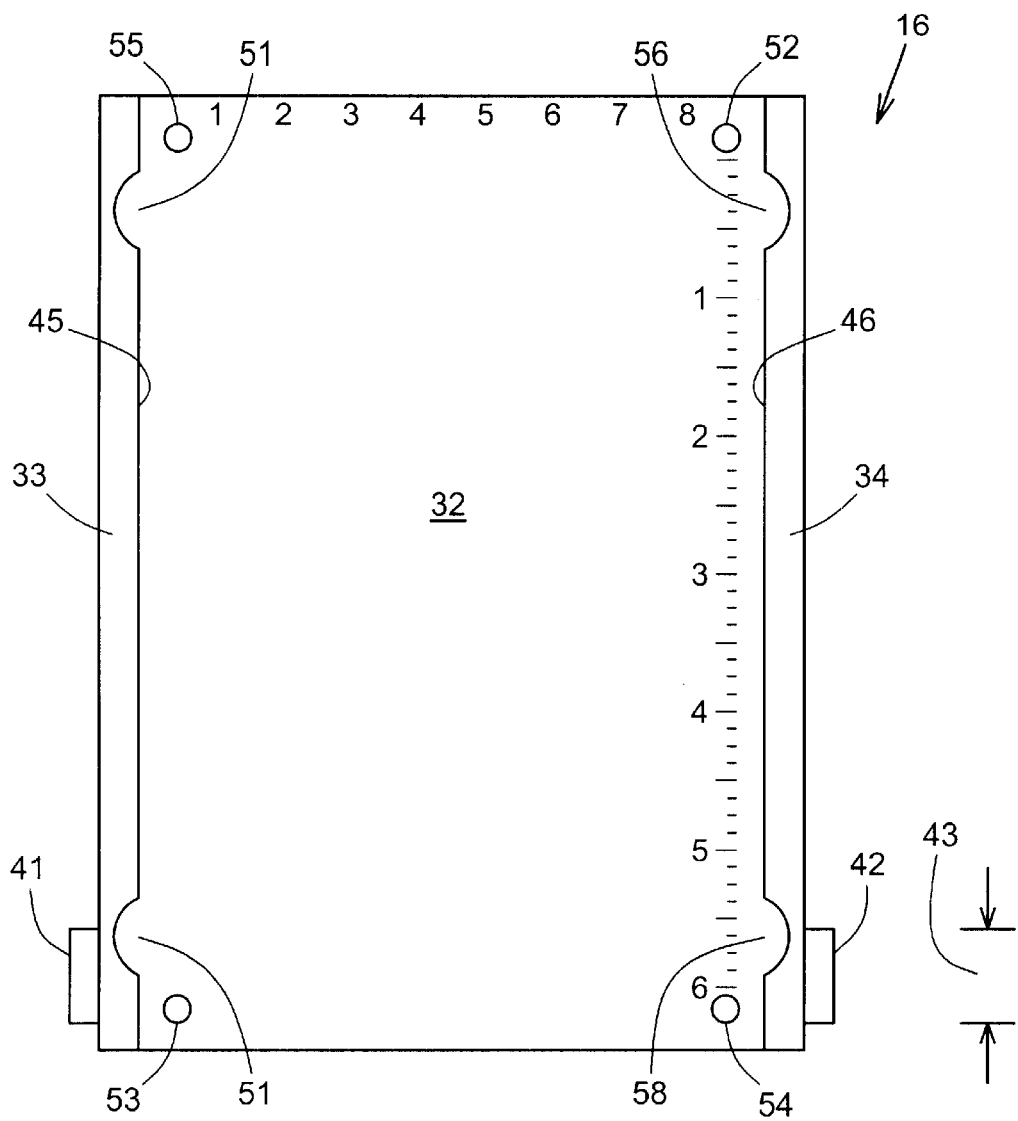
FIG. 3 is a top view of the tray of FIG. 2 showing the features of the invention.

FIG. 3 is a top view of the tray 16 alone. Extending outward from each of the two raised walls 33, 34 are tabs 41, 42. When the tray (and accompanying precast gel) is inserted into the tank, the tabs fit inside two of the grooves 27, 29 and the fit between the tabs and grooves stabilizes the position of the tray by preventing the tray from drifting laterally. Since the grooves taper in width from top to bottom, the tab width 43 is less than the width of the corresponding groove at the top of the groove, which facilitates insertion of the tray. To prevent lateral drift, however, the width of the tab is approximately equal to the width of the groove at the height at which the tray rests on the raised platform 23 of the tank.

Figure 4:
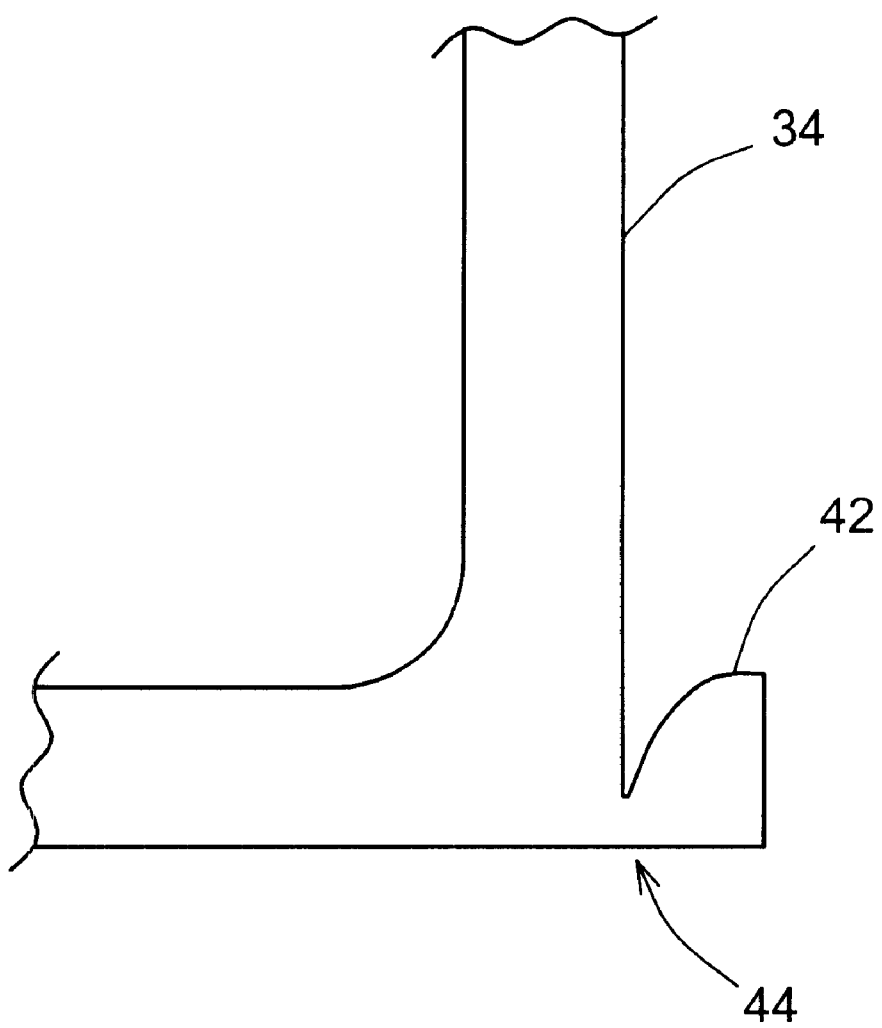
FIG. 4 is an enlarged end elevation view of one corner of the tray of FIG. 2 showing details of the tab construction.

In preferred embodiments of the invention, the tabs 41, 42 are removable by the user so that the precast gel can be used in electrophoresis cells whose tanks do not contain grooves on their inner wall surfaces such as those shown in FIG. 1. One method of achieving this versatility is shown in FIG. 4, which is an enlarged end view of one of the tabs 42. The tab 42 is joined to the outer surface of the raised wall 34 of the tray by a thin web 44 that allows the tab to be broken off by the manual pressure of the user.

A further feature of preferred embodiments of the invention, as shown in FIGS. 2 and 3, is a series of posts, pins, or protrusions 51, 52, 53, 54 extending upward from the tray base 32. The gel is cast around these posts, and the posts serve to prevent the gel from sliding along the tray base. The number of posts and their locations on the tray base are not critical and may vary. Preferably, four posts are included, one close to each of the four corners of the tray. The posts form indentations in the gel, but the indentations are small enough and close enough to the corners of the gel that they do not interfere with the migration of proteins through the gel during the electrophoresis. Further stabilization of the gel is provided by indentations 55, 56, 57, 58 in the inner surfaces of the side walls of the tray. Since the indentations are arc-shaped, the gel will be formed with protruding arc-shaped knobs extending into, and complementary in shape to, the indentations.

A still further feature of preferred embodiments of the invention is the inclusion of printed fluorescent indicia on the tray surface by hot foil stamping. As shown in FIG. 3, the indicia may indicate the lane numbers of the various samples (i.e., the numbers 1 through 8 near the top of the Figure at the location of one of the exposed edges of the gel), or the migration distance along the gel (as indicated by the ruler markings parallel to the right edge of the tray), or both. Hot foil stamping is a known printing technique in which a metallized stamping foil is transferred from a carrier film onto the tray surface by the application of heat and pressure, the foil containing an adhesive that is activated by heat. Metallized stamping foils for hot foil stamping are commercially available from suppliers in the printing industry. One such supplier is Foilmark, Inc., of Newburyport, Mass., USA (www.foilmark.com). This aspect of the invention resides in the discovery that indicia printed onto the gel tray by hot foil stamping is fluorescent and can be visualized as part of a fluorescent image that is generated when the protein spots are stained with a fluorescent dye. Preferably, the indicia are printed on the underside of the tray.

The materials of construction of the various elements of this invention are not critical to the invention and can vary widely. The tray is preferably made of a chemically inert, transparent material, such as polycarbonate or other plastics commonly used in electrophoresis cells. The gel, as mentioned above, is preferably agarose, but polyacrylamide and other gels may be used as well.

The foregoing descriptions are offered for purposes of illustration. Modifications and substitutions of the various elements, their dimensions, shapes, and configurations, which also fall within the scope of the invention, will be apparent to those skilled in the art upon reading these descriptions.

What is claimed is:

1. A precast electrophoresis slab gel and tray combination for use in horizontal submerged gel electrophoresis in an electrophoresis cell having an internal wall with a vertical groove, said combination comprising:

a tray having a flat base and raised walls on exactly two opposing sides of said base;

a tab protruding from the exterior surface of one of said raised walls, said tab sized to be received by said vertical groove and when thus received to prevent lateral movement of said tray; and an electrophoresis gel retained in said tray.

2. A combination in accordance with claim 1 comprising a first tab protruding from the exterior surface of one of said raised walls and a second tab protruding protruding from the exterior surface of the other of said raised walls, said first and second tabs arranged to be received by first and second vertical grooves respectively on opposing internal walls of said electrophoresis cell.

3. A combination in accordance with claim 1 in which said tab is joined to said exterior surface in a manner permitting complete removal of said tab from said surface by finger force alone.

4. A combination in accordance with claim 1 in which said vertical groove has a width decreases linearly downward from a width at an upper end of said groove the exceeds the width of said tab, the width of said tab substantially equaling the width of said vertical groove at a preselected height within said electrophoresis cell.

5. A precast electrophoresis slab gel and tray combination in accordance with claim 1 further comprising:

indicia identifying individual sample lanes, migration length, or both, printed on said flat base by hot stamp foil printing.

6. A combination in accordance with claim 5 in which said indicia are printed on the underside of said tray.

7. A precast electrophoresis slab gel and tray combination for use in horizontal submerged gel electrophoresis, said combination comprising:

a tray having a flat rectangular base and raised walls on exactly two opposing sides of said base and a plurality of posts extending upward from base; and an electrophoresis gel retained in said tray such that said posts are embedded in said gel.

8. A combination in accordance with claim 7 which said plurality of posts comprises posts wherein at least one post is in close proximity to each of the four corners of said flat rectangular base.

* * * * *